(12) United States Patent
Hu et al.

(10) Patent No.: US 12,419,340 B2
(45) Date of Patent: Sep. 23, 2025

(54) MICROBIAL FERMENTATION METHOD FOR IMPROVING TOBACCO QUALITY

(71) Applicant: Yunnan Academy of Tobacco Agricultural Sciences, Kunming (CN)

(72) Inventors: Binbin Hu, Kunming (CN); Jing Mai, Kunming (CN); Mingjun Zhu, Kunming (CN); Congming Zou, Kunming (CN); Zhonglong Lin, Kunming (CN); Ying Ning, Kunming (CN); Yi Chen, Kunming (CN); Yonglei Jiang, Kunming (CN); Ling Zou, Kunming (CN); Guiyan Zhou, Kunming (CN); Baoxing Wang, Kunming (CN); Jieyun Cai, Kunming (CN); Haowei Sun, Kunming (CN); Ke Zhang, Kunming (CN); Xiaowei Zhang, Kunming (CN)

(73) Assignee: Yunnan Academy of Tobacco Agricultural Sciences, Kunming (CN)

( * ) Notice: Subject to any disclaimer, the term of this patent is extended or adjusted under 35 U.S.C. 154(b) by 442 days.

(21) Appl. No.: 17/952,611

(22) Filed: Sep. 26, 2022

(65) Prior Publication Data

US 2023/0389594 A1    Dec. 7, 2023

(30) Foreign Application Priority Data

Jun. 6, 2022   (CN) .......................... 202210628009.1

(51) Int. Cl.
   A24B 15/20    (2006.01)
   C12N 1/20    (2006.01)
   C12P 1/04    (2006.01)

(52) U.S. Cl.
   CPC ................ *A24B 15/20* (2013.01); *C12N 1/20* (2013.01); *C12P 1/04* (2013.01)

(58) Field of Classification Search
   CPC .......... A24B 15/18; A24B 15/20; C12N 1/20; C12P 1/04
   See application file for complete search history.

(56) References Cited

U.S. PATENT DOCUMENTS 4,038,993 A * 8/1977 Geiss ..................... A24B 15/20
                                                        435/267
2016/0331020 A1* 11/2016 Marshall ................ A24B 15/30

FOREIGN PATENT DOCUMENTS

CN          109330008 A  *  2/2019  ............. A24B 15/24

OTHER PUBLICATIONS

CN109330008A English Translation obtained from Espacenet, pp. 1-9. (Year: 2025).*

* cited by examiner

*Primary Examiner* — Philip Y Louie
*Assistant Examiner* — Yared Tarekegn Kokeb
(74) *Attorney, Agent, or Firm* — Nitin Kaushik

(57) ABSTRACT

A microbial fermentation method for improving tobacco quality, comprising the following steps: (1) inoculating flue-cured tobacco as an inoculation source into a tobacco powder medium, and cultivating at 20-40° C. for 20-50 h; (2) inoculating microbial liquid in step (1) into a fresh tobacco powder medium, cultivating at 20-40° C. for 20-50 h, and circulating for 15-25 cycles to obtain stable flue-cured tobacco microbial flora; (3) inoculating the microbial flora obtained in step (2) into the fresh tobacco powder medium, and culturing at 20-40° C. for 20-50 h to obtain seed liquid of the microbial flora; (4) centrifuging the microbial liquid obtained in step (3) and collecting microbes; (5) washing the microbes collected in step (4); (6) resuspending the washed bacteria in step (5) to obtain a microbial suspension; and (7) spraying the microbial suspension in step (6) to the tobacco leaves for fermentation for 6-8 days.

9 Claims, 1 Drawing Sheet

MICROBIAL FERMENTATION METHOD FOR IMPROVING TOBACCO QUALITY

CROSS-REFERENCE TO RELATED APPLICATION

This application claims priority to and the benefit of Chinese Application No. 202210628009.1 filed Jun. 6, 2022. The entire disclosure of Chinese Application No. 202210628009.1 is incorporated herein by reference.

TECHNICAL FIELD

The present invention belongs to the technical field of tobacco, and particularly relates to a fermentation method for improving tobacco quality.

BACKGROUND

A number of microbes are present on leaves of flue-cured tobacco, and the natural aging process of the tobacco mainly relies on them to produce various enzymes and metabolites to improve the quality of tobacco. Natural aging can significantly improve the quality of tobacco, but takes a long time, which is usually 1-3 years, and is susceptible to the external environment, thus, the production cost is difficult to estimate. However, the method of fermentation by artificial inoculation of microbes can not only shorten the fermentation time to 1-2 weeks, but also effectively improve the quality of tobacco. At present, there are two major kinds of artificially inoculated microbes: the microbes isolated from tobacco that can degrade starch, cellulose, protein and so on and can change tobacco quality, and the aroma-producing microbes that can improve the aroma. Whereas, most of the microbes for artificial inoculation are single strains, which can only improve the quality of tobacco in some aspect.

SUMMARY

In order to solve the technical problems of long natural aging and fermentation time and single quality improvement by artificial inoculation of microbes in the prior art, the present invention provides a microbial fermentation method for improving tobacco quality.

The technical scheme of the present invention is as follows:

A microbial fermentation method for improving tobacco quality, characterized by comprising the following steps:
(1) inoculating the flue-cured tobacco as the inoculation source to a tobacco powder medium, and cultivating at 20-40° C. for 20-50 h;
(2) inoculating the microbial liquid in step (1) into a fresh tobacco powder medium, cultivating at 20-40° C. for 20-50 h, and circulating for 15-25 cycles to obtain stable flue-cured tobacco microbial flora;
(3) inoculating the microbial flora obtained in step (2) into a fresh tobacco powder medium, and cultivating at 20-40° C. for 20-50 h to obtain seed liquid of the microbial flora;
(4) centrifuging the microbial liquid obtained in step (3) and collecting microbes;
(5) washing the microbes collected in step (4);
(6) resuspending the washed microbes in step (5) to obtain a microbial suspension; and
(7) spraying the microbial suspension of step (6) on the tobacco leaves for fermenting for 6-8 days.

Preferably, in step (2), the cultivation is performed at the temperature of step (1) for the same time.

Preferably, in step (3), the cultivation is performed at the temperature of step (1) for the same time.

Preferably, after the step (2) is completed, the structure of the microbial flora obtained in step (2) is analyzed to obtain the relative abundance information of the top 10 species at the genus level.

Preferably, in step (1), the cultivation is performed at 37° C. for 24 h.

Preferably, in step (1), the cultivation is performed at 25° C. for 48 h.

Preferably, in step (2), circulation is performed for 20 cycles.

Preferably, in step (7), fermentation is performed for 7 days.

Preferably, in step (1), the tobacco powder medium comprises 8-12 g/L of tobacco powder, 8-12 g/L of tryptone, 4-6 g/L of yeast powder and 4-6 g/L of sodium chloride;

Preferably, in step (1), the tobacco powder is pulverized into powder at a low temperature and passes through a 200-mesh sieve.

The present invention has the beneficial effects as follows:

tobacco leaves are fermented by means of microbial flora enriched and domesticated from flue-cured tobacco. The microbial flora not only contains a large number of microbes capable of improving chemical components such as reducing sugar, protein, starch and nicotine in tobacco, but also contains a variety of microbes capable of increasing tobacco aroma quality and aroma quantity, and thus can improve the quality of tobacco in many ways.

The microbes in the flue-cured tobacco of the present invention can be enriched and domesticated at the growth temperature of 20-50° C., and various qualities can be optimized at different temperatures for different time periods.

By means of the fermentation parameters selected by the present invention, especially the preferred medium components, various qualities such as smoke volume, aroma, impact and coordination can be improved in a short period of time.

DETAILED DESCRIPTION OF THE EMBODIMENTS

In order to better clarify the purpose, technical scheme and advantages of the examples of the present invention, the technical scheme in the examples of the present invention will be clearly and completely illustrated below with reference to the drawings in the examples of the present invention. Clearly, the described examples are part of those of the present invention instead of all. Based on the examples of the present invention, all other examples obtained by those of ordinary skill in the art without creative efforts shall fall within the protection scope of the present invention.

Example 1

Figure 1:
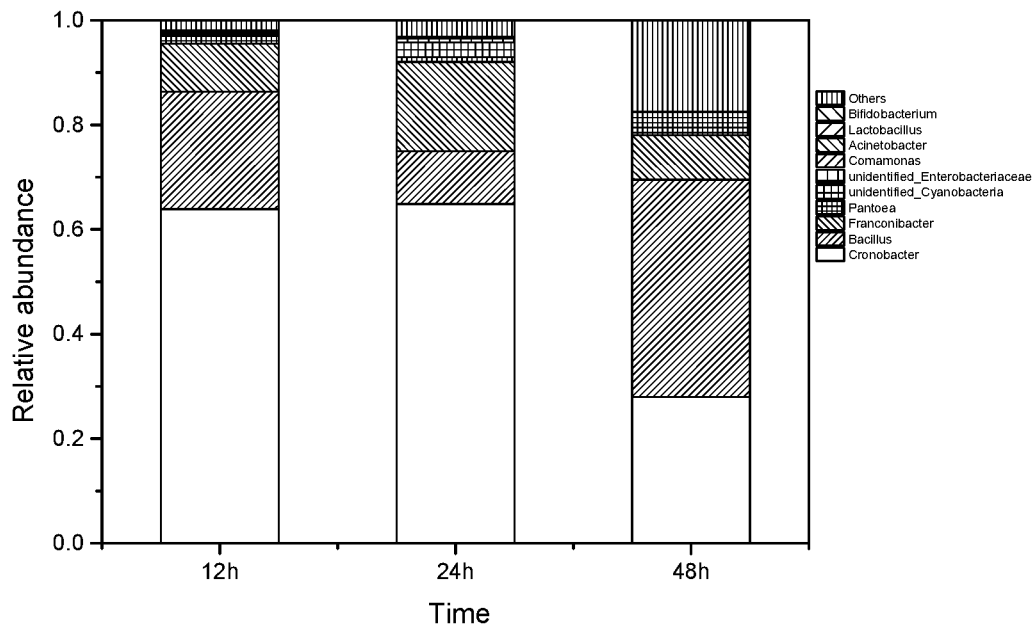
FIG. 1 is a graph showing the relative abundance of the top 10 species at the genus level of the microbial flora obtained by enrichment and domestication for different cultivation time in Example 1.

Tobacco leaves fermented by microbial flora of flue-cured tobacco at 37° C.:

(1) Enrichment of microbial flora of flue-cured tobacco at 37° C.: the flue-cured tobacco was inoculated into a tobacco powder medium as an inoculum source, and cultured at 37° C. for 24 h; the tobacco powder medium comprises 10 g/L of tobacco powder, 10 g/L of tryptone, 5 g/L of yeast powder and 5 g/L of sodium chloride;

(2) Domestication of microbial flora of flue-cured tobacco at 37° C.: the microbial liquid in step (1) was inoculated into a fresh tobacco powder medium, cultivated continuously at 37° C. for 24 h, and circulated for 20 cycles to obtain stable flue-cured tobacco microbial flora;

Structural analysis of the microbial flora: the structure of the microbial flora of flue-cured tobacco at 37° C. was analyzed by high-throughput sequencing technology, and the relative abundance information of the top 10 species at the genus level was obtained. As shown in FIG. 1, the three genera with the highest relative abundance are Cronobacter (*Cronobacter* spp.), Bacillus (*Bacillus* spp.) and Franconibacter (*Frankia*).

(3) Preparation of seed liquid: the microbial flora obtained in step (2) was inoculated into a fresh tobacco powder medium, and cultivated at 37° C. for 24 h to obtain seed liquid of the microbial flora at 37° C.;

(4) Centrifugation: the microbial liquid obtained in step (3) was centrifuged at rotating speed of 8000 g for 5 min to collect microbes;

(5) Washing: deionized water was added to the microbes collected in step (4) for washing, and step (4) was repeated twice;

(6) Resuspending: the washed microbes in step (5) was resuspended with deionized water to obtain a microbial suspension;

(7) Tobacco leaf fermentation: 0.4 mL/g of bacterial suspension was sprayed to the tobacco leaves, and the tobacco leaves were placed in an environment of 37° C. for 7 days of fermentation.

Analysis of principal chemical components of tobacco leaves: the contents of total sugar, reducing sugar, starch, protein and nicotine in tobacco leaves before and after fermentation were determined by a continuous flow method. The results are shown in Table 1. After fermentation, the content of total sugar and reducing sugar in tobacco leaves increased by 29.83% and 52.21%, respectively, while starch, protein and nicotine decreased by 32.55%, 10.05% and 43.71%, respectively;

Analysis of aroma components of tobacco leaves: the content of aroma components in tobacco leaves before and after fermentation were determined by a GC/MS fingerprint method. The results are shown in Table 2. The content of aroma components in the fermented tobacco leaves increased, and aldehydes, alcohols, ketones, lipids, alkenes, alkanes and derivatives thereof increased by 2.46, 1.88, 0.64, 1.69, and 2.96 times, respectively;

Preparation and inhaling evaluation of heat-not-burn cigarettes: the fermented tobacco leaves were prepared into heat-not-burn cigarettes (Heat-not-burn cigarettes) by the slurry process for papermaking, and inhaling evaluation experts were invited to inhale the smoke and evaluate the smoking. The inhaling evaluation results are shown in Table 3. After inhaling evaluation, it was found that the impact of the fermented tobacco leaves significantly increased, the coke aroma was stronger, the aroma was rich, and characteristics were apparent. The smoke volume, aroma, impact and coordination increased by 0.5, 0.5, 1.0 and 0.5 scores, respectively.

TABLE 1

Changes of principal chemical components in tobacco leaves before and after fermentation at 37° C.

| Sample | Principal chemical components | | | | |
|---|---|---|---|---|---|
| | Total sugar | Reducing sugar | Starch | Protein | Nicotine |
| Raw tobacco leaves | 30.41 | 24.40 | 5.53 | 5.57 | 3.50 |
| Fermented tobacco leaves | 39.48 | 37.14 | 3.73 | 5.01 | 1.97 |

TABLE 2

Changes of aroma components in tobacco leaves before and after fermentation at 37° C.

| Type | Aroma components | Content (µg/g) | |
|---|---|---|---|
| | | Raw tobacco leaves | Fermented tobacco leaves |
| Aldehydes | Phenylacetaldehyde | 0.63 | 2.31 |
| | n-pentadecanal | 0.23 | 0.85 |
| | 4-pentenal | 0.13 | 0.12 |
| | 3-methoxybenzaldehyde | 0.09 | 0.42 |
| | 4-diethylaminobenzaldehyde oxime | 0.09 | 0.15 |
| | 2,4-heptadienal | 0.01 | 0.27 |
| Total | 6 kinds | 1.19 | 4.12 |
| Alcohols | Cembrenediol 4 | 9.17 | 7.04 |
| | Cembrenediol 3 | 3.35 | 1.82 |
| | Phenylethanol | 1.62 | 3.73 |
| | Phytol | 1.62 | 4.86 |
| | Cembrenediol 2 | 1.42 | 2.51 |
| | Cembrenediol 1 | 0.60 | 0.86 |
| | Geranylgeraniol | 0.60 | 0.76 |
| | Black pinitol | 0.49 | 0.80 |
| | Bicyclo[2.2.1]hept-2,5-dien-7-ol | 0.13 | 0.23 |
| | Linalool | 0.09 | 0.38 |
| | Farnesol | 0.07 | 0.17 |
| | Benzyl alcohol | 0.03 | 3.98 |
| Total | 12 kinds | 19.19 | 27.14 |
| Ketones | Solanone | 6.09 | 14.43 |
| | β-damascenone | 2.96 | 9.83 |
| | Megastigmatrienone B | 1.66 | 5.05 |
| | Megastigmatrienone D | 1.24 | 4.49 |
| | Geranylacetone | 1.17 | 2.89 |
| | Megastigmatrienone C | 0.76 | 1.12 |
| | Megastigmatrienone A | 0.40 | 0.86 |
| | 5,6-dimethyl-2-benzimidazole | 0.33 | 3.51 |
| | 1-[4-(1-methyl-2-propenyl)phenyl]ethanone | 0.31 | 0.42 |
| | 4-hydroxy-β-damascenone | 0.28 | 1.25 |
| | β-damascenone | 0.16 | 0.51 |
| | Damascenone | 0.09 | 0.16 |
| | 4-oxoisophorone | 0.09 | 0.16 |
| | 1-ethyl-6-methyl-2(1H)-pyridone | 0.03 | 0.10 |
| Total | 14 kinds | 15.56 | 44.78 |
| Phenols | 2,6-di-tert-butyl-p-cresol | 4.74 | 2.25 |
| | 2,5-diethylphenol | 0.35 | 0.36 |

TABLE 2-continued

Changes of aroma components in tobacco leaves before and after fermentation at 37° C.

| Type | Aroma components | Raw tobacco leaves Content (μg/g) | Fermented tobacco leaves Content (μg/g) |
|---|---|---|---|
| | 2,6-dimethylphenol | 0.25 | 0.33 |
| | 4-vinyl-2-methoxyphenol | 0.12 | 2.51 |
| Total Lipids | 4 kinds | 5.47 | 5.45 |
| | Dibutyl phthalate | 2.31 | 1.61 |
| | Methyl palmitate | 1.38 | 3.08 |
| | Dihydroactinidiolide | 0.39 | 2.02 |
| Total Olefins | 3 kinds | 4.09 | 6.71 |
| | Neophytadiene | 142.93 | 414.32 |
| | Caryophyllene oxide | 4.14 | 5.02 |
| | Aromadendrene | 3.91 | 1.04 |
| | Artemisia triene | 2.20 | 1.15 |
| | β-elemene | 1.62 | 0.37 |
| | Alloaromadendrene | 1.42 | 1.05 |
| | Longifolene | 0.79 | 0.36 |
| | α-Selinene | 0.67 | 0.44 |
| | (E)-(β)-Farnesene | 0.51 | 2.87 |
| | γ-terpinene | 0.46 | 0.40 |
| | 3-tetradecene | 0.37 | 0.25 |
| | 1,4-octadiene | 0.07 | 0.24 |
| | Longifolene | 0.07 | 0.19 |
| | Pinene | 0.04 | 0.10 |
| Total | 14 kinds | 159.19 | 427.80 |
| Alkanes and their derivatives | m-cymene | 1.05 | 4.47 |
| | n-tridecane | 0.33 | 0.34 |
| | 1-allyl-3-methylene-cyclohexane | 0.23 | 0.39 |
| | 7-isopropyl-1-methylnaphthalene | 0.21 | 0.23 |
| | 2-bromohexane | 0.10 | 0.11 |
| | 6,6-dimethyl-3-methylenebicyclo[3.1.1]heptane | 0.05 | 1.23 |
| | 1,2-dihydro-1,4,6-trimethylnaphthalene | 0.05 | 1.23 |
| Total | 7 kinds | 2.02 | 8.00 |
| Nitrogenous chemicals | Myosming | 1.07 | 0.52 |
| | 1,5,8-trimethyltetraline | 0.39 | 0.17 |
| | 4-hexyloxyaniline | 0.23 | 0.94 |
| | 1,2,3,4-tetrahydroquinoxaline | 0.18 | 0.24 |
| | Indole | 0.15 | 0.27 |
| | Pyrrole | 0.07 | 0.11 |
| Total | 6 kinds | 2.09 | 2.25 |

TABLE 3

Sensory quality index scores of tobacco leaves before and after fermentation at 37° C.

| Sample group | Smoke volume | Aroma | Impact | Harmony | Pungency | Taste | Total | Description of sensory quality |
|---|---|---|---|---|---|---|---|---|
| Raw tobacco leaves | 8.0 | 23.0 | 7.0 | 7.5 | 13.5 | 22.5 | 81.5 | Thin aroma, low impact and poor fragrance |
| Fermented tobacco leaves | 8.5 | 23.5 | 8.0 | 8.0 | 13.0 | 22.5 | 83.5 | Obviously increased impact, heavier coke aroma, rich fragrance and apparent characteristics |

Example 2

Figure 2:
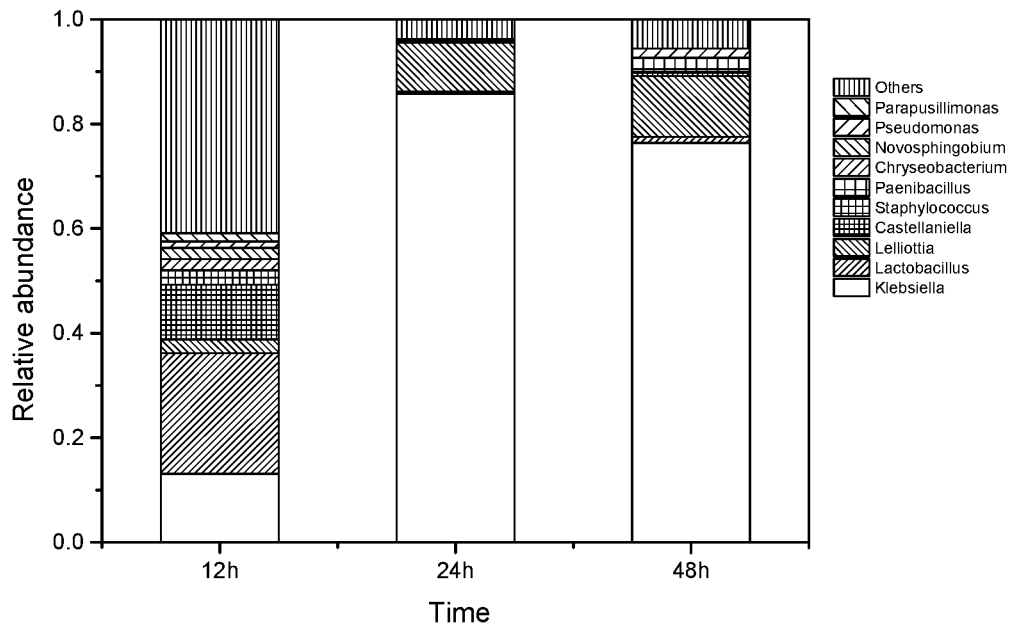
FIG. 2 is a graph showing the relative abundance of the top 10 species at the genus level of the microbial flora obtained by enrichment and domestication for different cultivation time in Example 2.

Tobacco leaves fermented by microbial flora of flue-cured tobacco at 25° C.:
  (1) enrichment of the microbial flora of flue-cured tobacco at 25° C.: inoculating the flue-cured tobacco as the inoculation source to a tobacco powder medium for cultivation at 25° C. for 48 h;
  (2) Domestication of microbial flora of flue-cured tobacco at 25° C.: the microbial liquid in step (1) was inoculated into a fresh tobacco powder medium, cultivated continuously at 25° C. for 48 h, and circulated for 20 cycles to obtain stable flue-cured tobacco microbial flora;

Structural analysis of the microbial flora: the structure of the microbial flora of flue-cured tobacco at 25° C. was analyzed by high-throughput sequencing technology, and the relative abundance information of the top 10 species at the genus level was obtained. As shown in FIG. 2, the three genera with the highest relative abundance are Klebsiella (Klebsiella spp.), Lactobacillus (Lactobacillus spp.) and Lelliottia, respectively.
  (3) Preparation of seed liquid: the microbial flora obtained in step (2) was inoculated into a fresh tobacco powder medium, and cultivated at 25° C. for 48 h to obtain the seed liquid of the microbial flora at 25° C.;
  (4) Centrifugation: the microbial liquid obtained in step (3) was centrifuged at rotating speed of 8000 g for 5 min to collect microbes;
  (5) Washing: deionized water was added to wash the microbes collected in step (4), and step (4) was repeated twice;
  (6) Resuspending: the washed microbes in step (5) was resuspended with deionized water to obtain a microbial suspension;
  (7) Tobacco leaf fermentation: 0.4 mL/g of bacterial suspension was sprayed into the tobacco leaves, and the tobacco leaves were placed in an environment of 25° C. for 7 days of fermentation.

Analysis of principal chemical components of tobacco leaves: the contents of total sugar, reducing sugar, starch, protein and nicotine in tobacco leaves before and after fermentation were determined by a continuous flow method. The results are shown in Table 4. After fermentation, the content of total sugar and reducing sugar in tobacco leaves increased by 20.45% and 42.92%, respectively, while starch, protein and nicotine decreased by 61.12%, 22.80% and 65.43%, respectively;

Analysis of aroma components of tobacco leaves: the content of aroma components in tobacco leaves before and after fermentation were determined by a GC/MS fingerprint method. The results are shown in Table 5. The content of aroma components in the fermented tobacco leaves increased substantially, and aldehydes, alcohols, ketones, lipids, alkenes, alkanes and derivatives and nitrogenous compounds thereof increased by 2.78, 0.57, 2.51, 1.03, 3.07, 7.27, 3.82, and 0.32 times, respectively;

Preparation and inhaling evaluation of heat-not-burn cigarettes: the fermented tobacco leaves were prepared into heat-not-burn cigarettes (Heat-not-burn cigarettes) by the slurry process for papermaking, and inhaling evaluation experts were invited to inhale the smoke and evaluate the smoking. The inhaling evaluation results are shown in Table 6. After inhaling evaluation, it was found that the smoke concentration of the fermented tobacco leaves increased, the impact was high, but the pungency rose, the aroma was single, and the smoke volume and the impact increased by 0.5 and 1.0 score, respectively.

TABLE 4

Changes of principal chemical components in tobacco leaves before and after fermentation at 25° C.

| | Principal chemical components | | | | |
| --- | --- | --- | --- | --- | --- |
| Sample | Total sugar | Reducing sugar | Starch | Protein | Nicotine |
| Raw tobacco leaves | 30.41 | 24.40 | 5.53 | 5.57 | 3.50 |
| Fermented tobacco leaves | 36.63 | 34.71 | 2.15 | 4.30 | 1.21 |

TABLE 5

Changes of aroma components in tobacco leaves before and after fermentation at 25° C.

| | | Content (μg/g) | |
| --- | --- | --- | --- |
| Type | Aroma components | Raw tobacco leaves | Fermented tobacco leaves |
| Aldehydes | Phenylacetaldehyde | 0.63 | 2.34 |
| | n-pentadecanal | 0.23 | 1.32 |
| | 4-pentenal | 0.13 | 0.13 |
| | 3-methoxybenzaldehyde | 0.09 | 0.20 |
| | 4-diethylamino-benzaldehyde oxime | 0.09 | 0.23 |
| | 2,4-heptadienal | 0.01 | 0.25 |
| Total | 6 kinds | 1.19 | 4.46 |
| Alcohols | Cembrenediol 4 | 9.17 | 6.36 |
| | Cembrenediol 3 | 3.35 | 1.41 |
| | Phenylethanol | 1.62 | 5.90 |
| | Phytol | 1.62 | 0.11 |
| | Cembrenediol 2 | 1.42 | 2.40 |
| | Cembrenediol 1 | 0.60 | 2.63 |
| | Geranylgeraniol | 0.60 | 0.87 |
| | Black pinitol | 0.49 | 2.92 |
| | Bicyclo[2.2.1]hept-2,5-dien-7-ol | 0.13 | 0.08 |
| | Linalool | 0.09 | 0.30 |
| | Farnesol | 0.07 | 0.01 |
| | Benzyl alcohol | 0.03 | 7.06 |
| Total | 12 kinds | 19.19 | 30.06 |
| Ketones | Solanone | 6.09 | 9.29 |
| | β-damascenone | 2.96 | 14.41 |
| | Megastigmatrienone B | 1.66 | 9.27 |
| | Megastigmatrienone D | 1.24 | 7.53 |
| | Geranylacetone | 1.17 | 2.82 |
| | Megastigmatrienone C | 0.76 | 1.62 |
| | Megastigmatrienone A | 0.40 | 2.25 |
| | 5,6-dimethyl-2-benzimidazole | 0.33 | 3.70 |
| | 1-[4-(1-methyl-2-propenyl)phenyl]ethanone | 0.31 | 0.44 |
| | 4-hydroxy-β-damascenone | 0.28 | 2.06 |
| | β-damascenone | 0.16 | 0.64 |
| | Damascenone | 0.09 | 0.36 |
| | 4-oxoisophorone | 0.09 | 0.08 |
| | 1-ethyl-6-methyl-2(1H)-pyridone | 0.03 | 0.19 |
| Total Phenols | 14 kinds | 15.56 | 54.66 |
| | 2,6-di-tert-butyl-p-cresol | 4.74 | 7.44 |
| | 2,5-diethylphenol | 0.35 | 0.33 |

TABLE 5-continued

Changes of aroma components in tobacco leaves before and after fermentation at 25° C.

| Type | Aroma components | Content (μg/g) Raw tobacco leaves | Content (μg/g) Fermented tobacco leaves |
|---|---|---|---|
| | 2,6-dimethylphenol | 0.25 | 0.35 |
| | 4-ethenyl-2-methoxyphenol | 0.12 | 2.96 |
| Total Lipids | 4 kinds | 5.47 | 11.08 |
| | Dibutyl phthalate | 2.31 | 7.45 |
| | Methyl palmitate | 1.38 | 6.67 |
| | Dihydroactinidiolide | 0.39 | 2.52 |
| Total Olefins | 3 kinds | 4.09 | 16.64 |
| | Neophytadiene | 142.93 | 1255.98 |
| | Caryophyllene oxide | 4.14 | 37.78 |
| | Aromadendrene | 3.91 | 6.42 |
| | Artemisia triene | 2.20 | 2.39 |
| | β-elemene | 1.62 | 0.56 |
| | Alloaromadendrene | 1.42 | 4.60 |
| | Longifolene | 0.79 | 0.06 |
| | α-Selinene | 0.67 | 0.77 |
| | (E)-(β)-Farnesene | 0.51 | 4.73 |
| | γ-terpinene | 0.46 | 0.46 |
| | 3-tetradecene | 0.37 | 2.23 |
| | 1,4-octadiene | 0.07 | 0.17 |
| | Longifolene | 0.07 | 0.23 |
| | Pinene | 0.04 | 0.12 |
| Total Alkanes and their derivatives | 14 kinds | 159.19 | 1316.50 |
| | m-cymene | 1.05 | 5.51 |
| | n-tridecane | 0.33 | 0.58 |
| | 1-allyl-3-methylene-cyclohexane | 0.23 | 0.22 |
| | 7-isopropyl-1-methylnaphthalene | 0.21 | 0.33 |
| | 2-bromohexane | 0.10 | 0.12 |
| | 6,6-dimethyl-3-methylenebicyclo[3.1.1]heptane | 0.05 | 1.49 |
| | 1,2-dihydro-1,4,6-trimethylnaphthalene | 0.05 | 1.49 |
| Total Nitrogenous chemicals | 7 kinds | 2.02 | 9.74 |
| | Myosming | 1.07 | 0.59 |
| | 1,5,8-trimethyltetraline | 0.39 | 0.19 |
| | 4-hexyloxyaniline | 0.23 | 1.17 |
| | 1,2,3,4-tetrahydroquinoxaline | 0.18 | 0.30 |
| | Indole | 0.15 | 0.44 |
| | Pyrrole | 0.07 | 0.05 |
| Total | 6 kinds | 2.09 | 2.75 |

TABLE 6

Sensory quality index scores of tobacco leaves before and after fermentation at 25° C.

| Sample group | Smoke volume | Aroma | Impact | Harmony | Pungency | Taste | Total | Description of sensory quality |
|---|---|---|---|---|---|---|---|---|
| Raw tobacco leaves | 8.0 | 23.0 | 7.0 | 7.5 | 13.5 | 22.5 | 81.5 | Thin aroma, low impact and poor fragrance |
| Fermented tobacco leaves | 8.5 | 23.0 | 8.0 | 7.5 | 13.0 | 22.5 | 82.5 | The smoke concentration increased, the impact is high, the pungency rose, and the aroma was single. |

In the aforementioned steps of the embodiment, the components of the tobacco powder culture medium described in step (1) are 10 g/L of tobacco powder, 10 g/L of tryptone, 5 g/L of yeast powder, and 5 g/L of sodium chloride.

The aforementioned are merely examples of the present invention. For those skilled in the art, this application can still modify the technical solutions described in the aforementioned embodiments, or equivalently replace some of the technical features. However, these modifications or substitutions do not make the essence of the corresponding technical solutions deviate from the spirit and scope of the technical solutions of various examples of the present invention.

The invention claimed is:

1. A microbial fermentation method for improving tobacco quality, comprising the following steps:
    (1) inoculating a flue-cured tobacco as an inoculation source into a tobacco powder medium and cultivating at 20-40° C. for 20-50 h to obtain a microbial liquid, wherein the tobacco powder medium comprises 8-12 g/L of tobacco powder, 8-12 g/L of tryptone, 4-6 g/L of yeast powder, and 4-6 g/L of sodium chloride;
    (2) inoculating the microbial liquid in step (1) into the tobacco powder medium, cultivating at 20-40° C. for 20-50 h, and circulating for 15-25 cycles to obtain stable flue-cured tobacco microbial flora;
    (3) inoculating the stable flue-cured tobacco microbial flora obtained in step (2) into the tobacco powder medium, and cultivating at 20-40° C. for 20-50 h to obtain seed liquid of the microbial flora;
    (4) centrifuging the seed liquid obtained in step (3) and collecting microbes;
    (5) washing the microbes collected in step (4);
    (6) resuspending the washed microbes in step (5) to obtain a microbial suspension; and
    (7) spraying the microbial suspension of step (6) on tobacco leaves for fermenting for 6-8 days.

2. The method according to claim 1, wherein in step (2), the cultivating is performed at the temperature of step (1) for the same amount of time.

3. The method according to claim 1, characterized in that in step (3), the cultivating is performed at the temperature of step (1) for the same amount of time.

4. The method according to claim 1, wherein after step (2) is completed, the structure of the stable flue-cured tobacco microbial flora obtained in step (2) is analyzed to obtain the relative abundance information of the top 10 species at the genus level.

5. The method according to claim 1, wherein in step (1), the cultivating is performed at 37° C. for 24 h.

6. The method according to claim 1, wherein in step (1), the cultivating is performed at 25° C. for 48 h.

7. The method according to claim 1, wherein in step (2), circulation is performed for 20 cycles.

8. The method according to claim 1, wherein in step (7), the fermentation is performed for 7 days.

9. The method according to claim 1, wherein in step (1), the tobacco leaves are pulverized into powder at a temperature of 0-10° C. and through a 200-mesh sieve.

* * * * *